US012778667B2

(12) United States Patent
Ebersole et al.

(10) Patent No.: US 12,778,667 B2
(45) Date of Patent: Nov. 3, 2026

(54) SURGICAL GRASPER WITH SURGICAL SMOKE EVACUATION AND VARIABLE FILTRATION

(71) Applicant: Covidien LP, Mansfield, MA (US)

(72) Inventors: Garrett P. Ebersole, Hamden, CT (US); Jacob C. Baril, Norwalk, CT (US)

(73) Assignee: Covidien LP, Mansfield, MA (US)

(*) Notice: Subject to any disclaimer, the term of this patent is extended or adjusted under 35 U.S.C. 154(b) by 1064 days.

(21) Appl. No.: 17/960,892

(22) Filed: Oct. 6, 2022

(65) Prior Publication Data

US 2024/0115309 A1 Apr. 11, 2024

(51) Int. Cl.

| | |
|---|---|
| ***A61B 17/29*** | (2006.01) |
| ***A61B 18/14*** | (2006.01) |
| *A61B 18/08* | (2006.01) |
| *A61M 1/00* | (2006.01) |

(52) U.S. Cl.
CPC ...... *A61B 18/1445* (2013.01); *A61B 17/2909* (2013.01); *A61B 2017/2903* (2013.01); *A61B 2017/2926* (2013.01); *A61B 18/085* (2013.01); *A61B 2217/005* (2013.01); *A61B 2218/008* (2013.01); *A61M 1/7411* (2021.05)

(58) Field of Classification Search
CPC ....... A61M 1/71–79; A61B 2017/2929; A61B 2218/007; A61B 2218/008; A61B 2217/005
See application file for complete search history.

(56) References Cited

U.S. PATENT DOCUMENTS

| | | | | |
|---|---|---|---|---|
| 5,217,460 | A | 6/1993 | Knoepfler | |
| 5,417,709 | A | 5/1995 | Slater | |
| 5,620,415 | A * | 4/1997 | Lucey | A61B 17/29 606/205 |
| 9,737,648 | B2 | 8/2017 | Mark et al. | |
| 10,959,771 | B2 | 3/2021 | Boudreaux et al. | |
| 2015/0080876 | A1 | 3/2015 | Worrell et al. | |
| 2015/0157390 | A1 | 6/2015 | Fleenor | |
| 2016/0114088 | A1* | 4/2016 | Minskoff | A61M 1/804 604/541 |
| 2017/0325878 | A1 | 11/2017 | Messerly et al. | |
| 2021/0068890 | A1 | 3/2021 | Baril et al. | |

FOREIGN PATENT DOCUMENTS

| | | | | |
|---|---|---|---|---|
| CN | 111329577 | A * | 6/2020 | A61B 18/12 |
| EP | 0007602 | A1 * | 2/1980 | A61M 1/7411 |

* cited by examiner

*Primary Examiner* — Nathan R Price
(74) *Attorney, Agent, or Firm* — Carter, DeLuca & Farrell, LLP

(57) ABSTRACT

A surgical grasper configured to evacuate fluids from a surgical site includes a housing defining an interior cavity and an elongated shaft extending distally from the housing and defining a lumen in fluid communication with the interior cavity defined by the housing. The surgical grasper also includes a distal cap disposed at a distal end of the elongated shaft and an end effector including a first jaw member and a second jaw member. The first and second jaw members have a distal portion configured to grasp tissue and a proximal portion pivotably coupled to the distal cap.

20 Claims, 4 Drawing Sheets

SURGICAL GRASPER WITH SURGICAL SMOKE EVACUATION AND VARIABLE FILTRATION

FIELD

The present disclosure relates to a surgical grasper and, more specifically, to a surgical grasper configured to evacuate and filter surgical smoke and other contaminants generated during performance of a surgical procedure.

BACKGROUND

Minimally invasive surgical procedures including both endoscopic and laparoscopic procedures permit surgery to be performed on organs, tissues and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula accessing the abdominal cavity to perform one or more surgical tasks. The cannula may incorporate a seal to establish a substantially fluid tight seal about the instrument to preserve the integrity of the pneumoperitoneum.

Instruments utilized during a laparoscopic procedure may include lasers, electro-cautery, or sonic cutting instruments, which produce smoke and/or an aerosol as a byproduct of treating tissue. Smoke plumes can obscure the clinician's field of vision and the odor generated is unpleasant. Further, the smoke plume may contain infectious agents which may contaminate the operating arena thereby presenting a danger to operating personnel. Chemical vapor may be irritating to the respiratory tract and also may be carcinogenic. The smoke, noxious fumes, and other gases and vapors can include particulates, bacteria, viral elements, and undesirable odors.

During a typical laparoscopic procedure, multiple devices are used to perform a combination of tasks including grasping/manipulating tissue and evacuating contaminated fluids such as smoke from the surgical site. The surgeon must perform these combination of tasks without losing focus on the tissue being treated at the surgical site. Therefore, it would be advantageous to provide a single surgical instrument configured to perform these multiple functions to improve surgeon performance and increase safety during a procedure.

SUMMARY

As used herein, the term "distal" refers to the portion that is being described which is further from an operator (whether a human surgeon or a surgical robot), while the term "proximal" refers to the portion that is being described which is closer to the operator. Terms including "generally," "about," "substantially," and the like, as utilized herein, are meant to encompass variations, e.g., manufacturing tolerances, material tolerances, use and environmental tolerances, measurement variations, design variations, and/or other variations, up to and including plus or minus 10 percent.

As used herein, the term "clinician" refers to any medical professional (i.e., doctor, surgeon, nurse, or the like) or other user involved in operation of the surgical system described herein.

As used herein, "exemplary" does not necessarily mean "preferred" and may simply refer to an example unless the context clearly indicates otherwise.

Provided in accordance with aspects of the present disclosure is a surgical grasper configured to evacuate fluids from a surgical site. The surgical grasper includes a housing defining an interior cavity, an elongated shaft extending distally from the housing, and a distal cap disposed at a distal end of the elongated shaft. The elongated shaft defines a lumen in fluid communication with the interior cavity defined by the housing. The surgical grasper also includes an end effector including a first jaw member and a second jaw member and at least one suction hole defined through the distal cap. Each of the first and second jaw members have a distal portion configured to grasp tissue and a proximal portion pivotably coupled to the distal cap. The at least one suction hole is in fluid communication with the lumen defined by the elongated shaft for evacuating fluid from a surgical site.

In an aspect of the present disclosure, the surgical grasper also includes a handle coupled to the housing and configured to pivot at least one of the first or second jaw members relative to the other jaw member to transition the end effector between a closed configuration wherein the first and second jaw members are approximated to grasp tissue and an open configuration wherein the first and second jaw members are spaced apart.

In another aspect of the present disclosure, the surgical grasper also includes a fluid flow path extending from the at least one suction hole, through the lumen defined by the elongated shaft, and through the interior cavity of the housing.

In another aspect of the present disclosure, the surgical grasper also includes a fluid port extending from an outer surface of the housing. The fluid port is configured to be coupled to a tube for placing the surgical grasper in fluid communication with a suction source.

In still another aspect of the present disclosure, the surgical grasper also includes a rotation knob configured to rotate the end effector and the distal cap relative to the elongated shaft about a longitudinal axis defined by the elongated shaft.

In yet another aspect of the present disclosure, the elongated shaft, the distal cap, and the end effector are configured to be inserted through a surgical access device inserted through patient tissue to access a peritoneal cavity.

In still yet another aspect of the present disclosure, the surgical grasper also includes a filter sleeve disposed within the lumen defined by the elongated shaft. The elongated shaft defines at least one first window configured to expose the filter sleeve.

In another aspect of the present disclosure, the surgical grasper also includes a rotatable sleeve coaxially surrounding the elongated shaft and configured to be rotated about a longitudinal axis defined by the elongated shaft. The rotatable sleeve defines at least one second window configured to be misaligned or at least partially aligned with the at least one first window to control fluid flow through the filter sleeve.

In still another aspect of the present disclosure, the surgical grasper also includes a rotation tab extending from the filter sleeve and configured for enabling a user to manually rotate the rotatable sleeve about a longitudinal axis defined by the elongated shaft.

In yet another aspect of the present disclosure, the surgical grasper is configured to be attached to a surgical robot arm of a robotic surgical system.

Another surgical grasper provided in accordance with the present disclosure includes a housing defining an interior cavity, an elongated shaft extending distally from the housing, and a filter sleeve disposed within the lumen defined by the elongated shaft and configured to filter fluid from a surgical site. The elongated shaft defines a lumen in fluid communication with the interior cavity defined by the housing. The surgical grasper also includes at least one first window extending longitudinally along at least a portion of the elongated shaft and an end effector including a first jaw member and a second jaw member. The at least one first window is configured to expose the filter sleeve and the first and second jaw members are configured to grasp tissue. The surgical grasper also includes a rotatable sleeve coaxially surrounding the elongated shaft and at least one second window extending longitudinally along at least a portion of the rotatable sleeve. The rotatable sleeve is configured to be rotated about a longitudinal axis defined by the elongated shaft. Rotation of the rotatable sleeve is configured to rotate the at least one second window into axial misalignment with the at least one first window to prevent fluid flow through the filter sleeve or at least partial axial alignment with the at least one first window to at least partially expose the filter sleeve for facilitating fluid flow through the filter sleeve.

In an aspect of the present disclosure, the surgical grasper also includes a handle coupled to the housing and configured to pivot at least one of the first or second jaw members relative to the other jaw member to transition the end effector between a closed configuration wherein the first and second jaw members are approximated to grasp tissue and an open configuration wherein the first and second jaw members are spaced apart.

In another aspect of the present disclosure, the surgical grasper also includes a fluid flow path extending from the filter sleeve, thorough the lumen defined by the elongated shaft, and through the interior cavity of the housing.

In still another aspect of the present disclosure, the surgical grasper also includes a fluid port extending from an outer surface of the housing. The fluid port defines a lumen in fluid communication with the interior cavity of the housing for evacuating filtered fluid from the surgical grasper.

In yet another aspect of the present disclosure, the surgical grasper also includes a rotation knob configured to rotate the end effector relative to the elongated shaft about a longitudinal axis defined by the elongated shaft.

In still yet another aspect of the present disclosure, the elongated shaft, the distal cap, and the end effector are configured to be inserted through a surgical access device inserted through patient tissue to access a peritoneal cavity.

Another surgical grasper provided in accordance with the present disclosure includes a housing defining an interior cavity, an elongated shaft extending distally from the housing and defining a lumen in fluid communication with the interior cavity defined by the housing, and a distal cap disposed at a distal end of the elongated shaft. An end effector includes a first jaw member and a second jaw member. Each of the first and second jaw members has a distal portion configured to grasp tissue and a proximal portion pivotably coupled to the distal cap. At least one suction hole is defined through the distal cap, and the at least one suction hole is in fluid communication with the lumen defined by the elongated shaft for evacuating fluid from a surgical site. A filter sleeve is disposed within the lumen defined by the elongated shaft and is configured to filter fluid from the surgical site.

In an aspect of the present disclosure, the surgical grasper also includes a rotatable sleeve coaxially surrounding the elongated shaft and configured to be rotated about a longitudinal axis defined by the elongated shaft to control fluid flow through the filter sleeve.

In another aspect of the present disclosure, the surgical grasper also includes at least one first window extending longitudinally along at least a portion of the elongated shaft and at least one second window extending longitudinally along at least a portion of the rotatable sleeve. The at least one first window is configured to expose the filter sleeve. Rotation of the rotatable sleeve is configured to rotate the at least one second window into axial misalignment with the at least one first window to prevent fluid flow through the filter sleeve or at least partial axial alignment with the at least one first window to at least partially expose the filter sleeve for facilitating fluid flow through the filter sleeve.

In still another aspect of the present disclosure, a rotation tab extends from the filter sleeve and is configured for enabling a user to manually rotate the rotatable sleeve about a longitudinal axis defined by the elongated shaft.

BRIEF DESCRIPTION OF THE DRAWINGS

The above and other aspects and features of this disclosure will become more apparent in view of the following detailed description when taken in conjunction with the accompanying drawings wherein like reference numerals identify similar or identical elements.

DETAILED DESCRIPTION

Particular embodiments of the present disclosure are described hereinbelow with reference to the accompanying drawings. However, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure.

The present disclosure relates to a surgical device for removing and/or filtering fluids from a surgical site within a patient (e.g., the peritoneal cavity), during a laparoscopic procedure. Such fluids may include blood, saline, smoke and other gaseous material in addition to aerosol and particle byproducts of the laparoscopic procedure involving cutting, heating, or burning, and may include, for example, chemicals, ultrasonic vapors, particles, and ion dust particles.

More particularly, the present disclosure relates to a surgical grasper that, in addition to performing standard tissue grasping functions, is configured to efficiently remove smoke, odor, vapor, particles, or plumes released by chemicals or produced by the use of lasers, sonic cutting and/or cautery or other surgical techniques or instruments, (hereinafter, collectively referred to as "contaminated fluids"), from within a surgical site such as, e.g., the peritoneal cavity of a patient.

Figure 1:
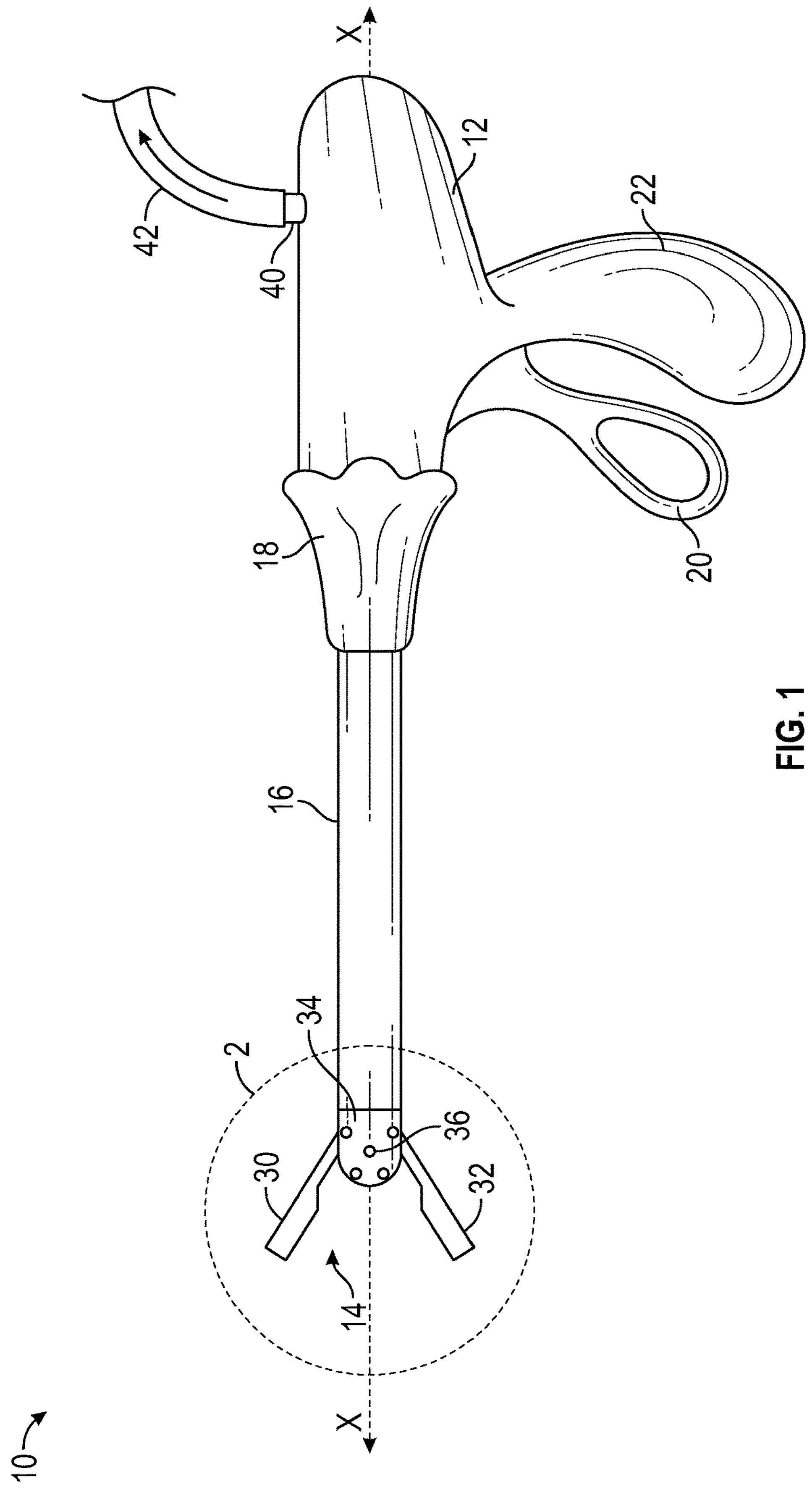
FIG. 1 is a perspective view of a surgical grasper in accordance with embodiments of this disclosure.
Figure 2:
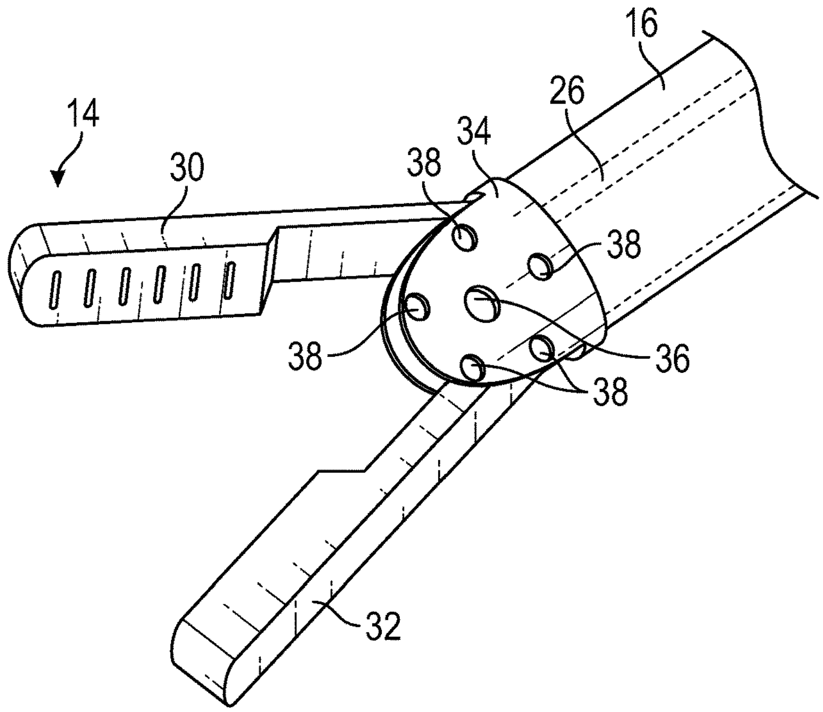
FIG. 2 is an enlarged isolated view of the area of detail of FIG. 1 depicting a distal portion of the surgical grasper of FIG. 1.
Figure 3:
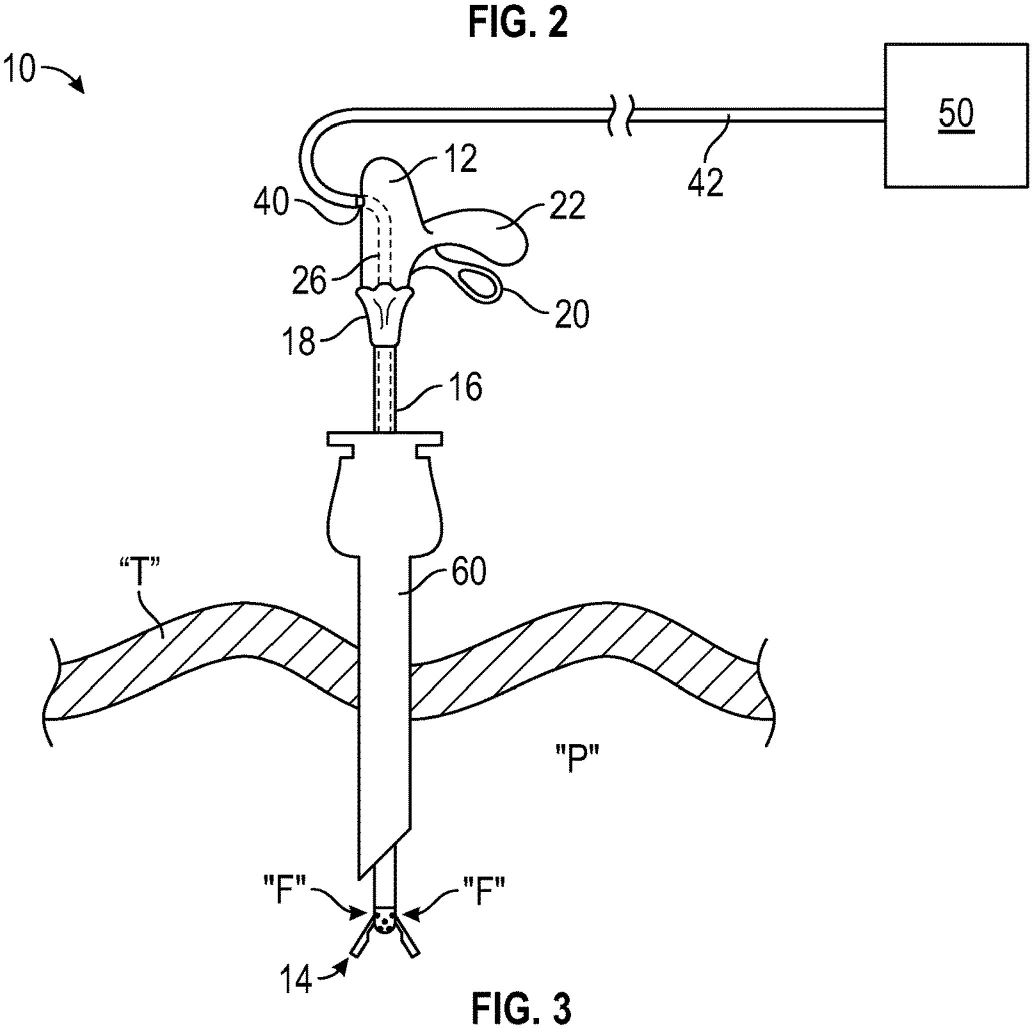
FIG. 3 shows an access device advanced into a peritoneal cavity and having the surgical grasper of FIG. 1 received through the access device.

Referring initially to FIGS. 1-3 there is illustrated a surgical grasper 10 adapted to couple to a suction source 50 (FIG. 3) to provide suction to a distal portion of the surgical grasper 10, thereby facilitating the evacuation of contaminated fluids from a surgical site within a patient (e.g., the peritoneal cavity) during a laparoscopic procedure according to an embodiment of this disclosure. The suction source 50 may be, for example, a smoke evacuator configured to generate suction. In aspects of this disclosure, the surgical grasper 10 may be of the disposable type that can be disposed of after a one-time use. Access to an insufflated peritoneal cavity during a laparoscopic procedure is provided by an access device 60 (FIG. 3) to permit the introduction of one or more surgical objects (e.g., graspers, electrosurgical devices, laparoscopic or endoscopic clip appliers, dissectors, retractors, staplers, laser probes, photographic devices, tubes, endoscopes and laparoscopes, and the like) for performing various surgical tasks on internal organs. For example, the surgical grasper 10 of this disclosure may access the peritoneal cavity via the access device 60 for performing multiple tasks including grasping and/or manipulating tissue within the peritoneal cavity and evacuating contaminated fluids from within the peritoneal cavity. In aspects of this disclosure, the surgical grasper 10 may include a filter or filter sleeve for filtering the contaminated fluids during removal of the contaminated fluids from the surgical site.

The surgical grasper 10 generally includes a housing 12 that supports various actuators for remotely controlling an end effector 14 disposed at a distal end of an elongated shaft 16 extending from the housing 12. The housing 12 may be configured as a handle including, for example, a pistol-style grip, although other handle configurations are also contemplated as are non-handle configurations, e.g., for mounting the surgical grasper 10 and/or attaching the surgical grasper 10 to a surgical robot arm (see FIG. 5). The elongated shaft 16 is tubular to define a lumen configured to receive one or more mechanical actuators operably coupling the end effector 14 to the various actuators supported by the housing 12.

To mechanically control the end effector 14, the housing 12 supports a movable handle 20 and a rotation knob 18. The movable handle 22 is operable to move the end effector 14 between an open configuration wherein a pair of opposed jaw members 30, 32 are disposed in spaced relation relative to one another, and a closed or clamping configuration wherein the jaw members 30, 32 are approximated to grasp tissue. Approximation of the movable handle 20 with a stationary handle 22 of the housing 12 serves to move the end effector 14 to the closed configuration and separation of the movable handle 20 from the stationary handle 22 serves to move the end effector 14 to the open configuration. Each of the jaw members include a distal portion configured to grasp tissue and a proximal portion pivotably coupled to a distal cap 34 disposed at a distal end of the elongated shaft 16. The distal cap 34 and the end effector 14 are rotatable relative to the elongated shaft 16 about a longitudinal axis X-X extending through the elongated shaft 16 via corresponding rotation of the rotation knob 18 about the longitudinal axis X-X. Included among the various actuators supported by the housing 12 may be an articulation actuator (not shown) operable to articulate the end effector 14 along at least one axis through various mechanisms including, for example, a series of joints, one or more hinges, and one or more cam or pulley systems.

The distal cap 34 supports a pivot pin 36 about which one or both jaw members 30, 32 pivot to move the end effector 14 between the open and closed configurations. However, other suitable configurations for facilitating movement of the end effector 14 between the open and closed configurations are contemplated. One or more suction holes 38 are formed through the distal cap 34 and are in fluid communication with the lumen defined by the elongated shaft 16. The one or more suction holes 38 may have various geometries such as, for example, circular, oval, complex shape, etc. The one or more suction holes 38 may be formed through both sides of the distal cap 34 for maximum suction or through only one side of the distal cap 34 for focusing suction to a particular side of the distal cap 34 and the end effector 14 depending on the rotated orientation of the distal cap 34. In aspects of this disclosure, an optional inline tube 26 (FIGS. 2 and 3) in fluid communication with the one or more suction holes 38 may extend from the distal cap 34 through the lumen defined by the elongated shaft 16 and the interior of the housing 12 for coupling to a fluid port 40 extending from an outer surface of the housing 12. In this respect, the inline tube 26 may serve as a fluid conduit through which contaminated fluids may be evacuated through the surgical grasper 10. In aspects of this disclosure, the lumen defined by the elongated shaft 16 may itself serve as a fluid conduit through which contaminated fluids may be evacuated from within the peritoneal cavity.

The fluid port 40 defines a lumen in fluid communication with the interior of the housing 12. As shown in FIG. 3, a tube 42 may be coupled to the fluid port 40 and serves to interconnect the fluid port 40 with a suction source 50 (FIG. 3) to place the interior of the housing 12 (or the inline tube 26) in fluid communication with the suction source 50 via the lumen defined by the fluid port 40. The suction source 50 may include a filter for filtering contaminated fluids received from the surgical grasper 10. The surgical grasper 10 may be inserted through an access device 60 (e.g., a cannula assembly) for passage through tissue "T" to access the peritoneal cavity "P", as shown in FIG. 3. A proximal portion of the elongated shaft 16 is received within the interior of the housing 12 such that the interior of the housing 12 may be in fluid communication with the lumen defined by the elongated shaft 16. A fluid flow path "F" is created through the surgical grasper 10, either through the inline tube 26 or through the components of the surgical grasper 10 itself, that starts at the one or more suction holes 38 and continues through the lumen defined by the elongated shaft 16, the interior of the housing 12, and the lumen defined by the fluid port 40. Thus, suction applied to the surgical grasper 10 by the suction source 50 serves to induce the evacuation of contaminated fluids through the suction holes 38 and along the fluid flow path "F" for ultimate evacuation of the contaminated fluids through the tube 42 and into the suction source 50 for filtration and release into the operating room. It is contemplated that during a procedure where fluid evacuation is not needed, the fluid port 40 may be capped to fluidly seal the fluid port 40 and the interior of the housing 12.

In some aspects of this disclosure, the housing 12 may support an actuator (not shown) in communication with the suction source 50 that is operable to remotely initiate and terminate operation of the suction source 50 and/or remotely control a flow rate of suction applied by the suction source 50. The actuator may be, for example, a button, a rocker switch, a slide switch, a dial, or the like.

Figure 4A:
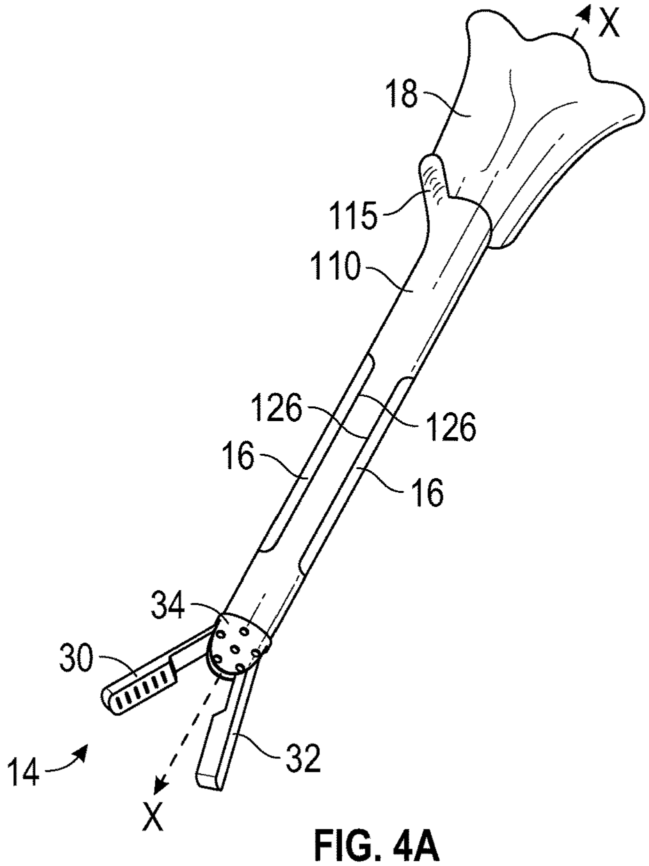
FIGS. 4A and 4B are perspective views of a portion of the surgical grasper of FIG. 1 depicting a rotatable sleeve of the surgical grasper rotated from a first configuration to a second configuration.
Figure 4B:
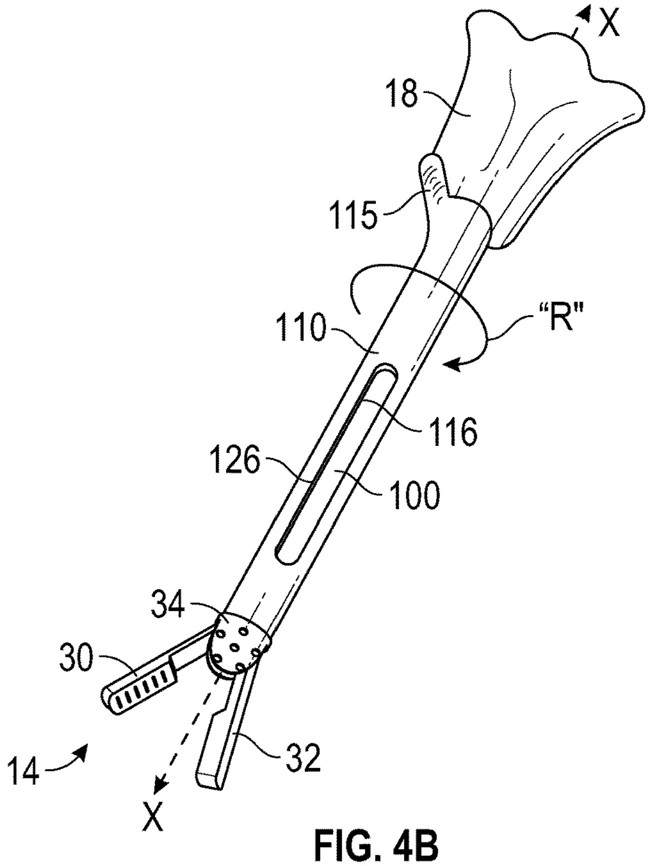

Referring now to FIGS. 4A and 4B, the surgical grasper 10 may include a filter sleeve 100 and a rotatable sleeve 110 coaxially surrounding the elongated shaft 16. The rotatable sleeve 110 is configured to rotate about the longitudinal axis X-X to control the rate of filtration by exposing more or less surface area of the filter sleeve 100. More specifically, the filter sleeve 100 is disposed within the lumen defined by the elongated shaft 16 and the elongated shaft 16 includes one or more windows 116 (FIG. 4B) extending longitudinally along at least a portion of the elongated shaft 16 to expose the filter sleeve 100 from within the elongated shaft 16. The elongated shaft 16 is coaxially received within the rotatable sleeve 110 such that the elongated shaft 16 and the rotatable sleeve 110 are concentric with respect to each other. The rotatable sleeve 110 includes one or more windows 126 extending longitudinally along at least a portion of the rotatable sleeve 110. The rotatable sleeve 110 includes a rotation tab 115 extending from a proximal end of the rotatable sleeve 110. The rotation tab 115 is suitable for enabling a user to manually rotate the rotatable sleeve 110 (e.g., by hand) about the longitudinal axis X-X.

With reference to FIG. 4A, the one or more windows 126 of the rotatable sleeve 110 are shown rotationally misaligned with the one or more windows 116 of the elongated shaft 16 (or otherwise aligned with an outer surface of the elongated shaft 16) such that the filter sleeve 100 is unexposed, thereby restricting fluid flow through the filter sleeve 100. As depicted in FIG. 4B, rotation of the rotatable sleeve 110 (e.g., via the rotation tab 115) about the longitudinal axis X-X, indicated by rotational arrow "R" in FIG. 4B, causes the one or more windows 126 to at least partially rotationally align with the one or more windows 116 of the elongated shaft 16, thereby at least partially exposing the filter sleeve 100. In this manner, fluid flow through the filter sleeve 100 can be controlled by rotation of the rotatable sleeve 110 relative to the elongated shaft 16. For example, the rotatable sleeve 110 may be rotated about the longitudinal axis X-X to selectively axially align, partially align, or axially misalign the windows 126 of the rotatable sleeve 110 with the windows 116 of the elongated shaft 16 to vary fluid flow through the filter sleeve 100, thereby controlling the level of filtration. For example, the windows 116, 126 may be aligned to expose the maximum surface area of the filter sleeve 100 for maximum fluid flow through the filter sleeve 100, partially aligned to expose less than the maximum surface area of the filter sleeve 100, or misaligned such that the filter sleeve 100 is mostly or completely unexposed to restrict fluid flow through the filter sleeve 100. Aligning or partially aligning the windows 116, 126 serves to provide airflow from the pressurized peritoneal cavity through the surgical grasper 10 via the elongated shaft 16 and the housing 12 with filtration occurring as the contaminated fluid travels along this path. Ultimately, the filtered airflow is released through the fluid port 40 extending from the housing 12 into the operating room. Alternatively, the filtered airflow may be actively evacuated through the fluid port 40 via suction applied to the surgical grasper 10 by the suction source 50 through the tube 42 coupled to the fluid port 40.

Figure 5:
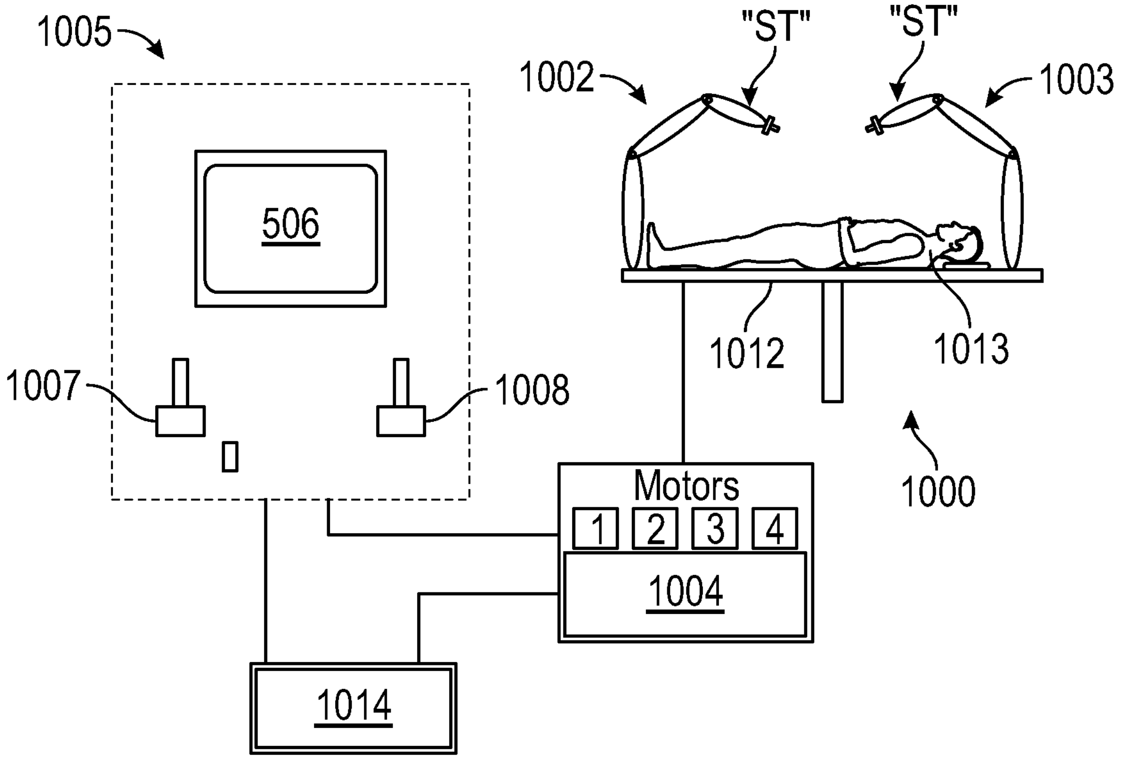
FIG. 5 is a schematic illustration of an exemplary robotic surgical system configured for use with the present disclosure.

In aspects of this disclosure, the surgical grasper 10 may include the suction holes 38 configuration of FIGS. 1-3 without the filter sleeve 100 configuration of FIGS. 4A-5. In other aspects of this disclosure, the surgical grasper 10 may include the filter sleeve 100 configuration of FIGS. 4A-5 but not the suction holes 38 configuration of FIGS. 1-3. In still other aspects of this disclosure, the surgical grasper 10 may include both the suction holes 38 configuration of FIGS. 1-3 and the filter sleeve 100 configuration of FIGS. 4A-5. In the aspect of the surgical grasper 10 including the filter sleeve 100 configuration of FIGS. 4A-5 without the suction holes 38 configuration of FIGS. 1-3, the filtration of contaminated fluids may be passive in that no suction is applied to the surgical grasper 10 by a suction device (e.g., suction source 50). In this scenario, contaminated fluids within the peritoneal cavity pass directly through the window(s) 120 formed through the rotatable sleeve 110 and through the filter sleeve 100. The resulting filtered air travels up the lumen defined by the elongated shaft 16, through the interior of the housing 12 and is released into the operating room via the fluid port 40. Thus, this configuration creates a fluid flow path through the surgical grasper 10 that starts at the exposed filter sleeve 110 and continues through the lumen defined by the elongated shaft 16, the interior of the housing 12, and the lumen defined by the fluid port 40.

The filter sleeve 100 may be an ultra-high molecular filter (or ULPA filter), activated carbon filter, a high efficiency particulate air filter (or HEPA filter), or a combination of two or more of them. In one example, the filter sleeve 100 includes a high-density polyethylene material (HDPE) or a polyurethane material, with activated charcoal. In embodiments, the filter sleeve 100 is capable of providing a flow rate of at least 6 liters per minute (at 15 mm mercury) from the peritoneal cavity through the filter. The filter can be capable of removing smoke and contaminant particles from the fluid including nanoparticles or ultrafine particles of less than 0.12 microns in diameter with an efficiency rate of least 99.995%. These particles may be responsible for causing systemic diseases as a result of chronic exposure in operating rooms to health care personnel. The filter may be an ultra-low particulate air filter (ULPA filter) with or without carbon or other odor reducing elements. The filter can include a combination of film, resins and/or activated carbon. In some embodiments, the filter can be comprised of multiple filters formed from different materials. For example, the filter may include a plurality of disc-shaped filters.

Turning to FIG. 5, a robotic surgical system 1000 configured for use in accordance with the present disclosure is shown. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and a mounted device which may be, for example, a surgical tool "ST." The surgical tools "ST" may include, for example, the surgical grasper 10 of the present disclosure, thus providing any of the above-detailed functionality on a robotic surgical system 1000.

Robot arms 1002, 1003 may be driven by electric drives, e.g., motors, connected to control device 1004. The motors, for example, may be rotational drive motors configured to provide rotational inputs to accomplish a desired task or tasks. Control device 1004, e.g., a computer, may be configured to activate the motors, in particular by means of a computer program, in such a way that robot arms 1002, 1003, and, thus, their mounted surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

Control device 1004, more specifically, may control one or more of the motors based on rotation, e.g., controlling to rotational position using a rotational position encoder (or Hall effect sensors or other suitable rotational position detectors) associated with the motor to determine a degree of rotation output from the motor and, thus, the degree of rotational input provided. Alternatively or additionally, control device 1004 may control one or more of the motors based on torque, current, or in any other suitable manner.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. A surgical grasper configured to evacuate fluids from a surgical site, comprising:

a housing defining an interior cavity;

an elongated shaft extending distally from the housing and defining a lumen in fluid communication with the interior cavity defined by the housing;

a distal cap disposed at a distal end of the elongated shaft;

an end effector including a first jaw member and a second jaw member, the first and second jaw members having a distal portion configured to grasp tissue and a proximal portion pivotably coupled to the distal cap, wherein the distal cap supports a pivot pin about which the first and second jaw members pivot; and at least one suction hole defined through the distal cap, the at least one suction hole in fluid communication with the lumen defined by the elongated shaft for evacuating fluid from a surgical site.

2. The surgical grasper according to claim 1, further comprising a handle coupled to the housing and configured to pivot at least one of the first or second jaw members relative to the other jaw member to transition the end effector between a closed configuration wherein the first and second jaw members are approximated to grasp tissue and an open configuration wherein the first and second jaw members are spaced apart.

3. The surgical grasper according to claim 1, further comprising a fluid flow path extending from the at least one suction hole, through the lumen defined by the elongated shaft, and through the interior cavity of the housing.

4. The surgical grasper according to claim 1, further comprising a fluid port extending from an outer surface of the housing, the fluid port configured to be coupled to a tube for placing the surgical grasper in fluid communication with a suction source.

5. The surgical grasper according to claim 1, further comprising a rotation knob configured to rotate the end effector and the distal cap relative to the elongated shaft about a longitudinal axis defined by the elongated shaft.

6. The surgical grasper according to claim 1, wherein the elongated shaft, the distal cap, and the end effector are configured to be inserted through a surgical access device inserted through patient tissue to access a peritoneal cavity.

7. The surgical grasper according to claim 1, further comprising a filter sleeve disposed within the lumen defined by the elongated shaft, the elongated shaft defining at least one first window configured to expose the filter sleeve.

8. The surgical grasper according to claim 7, further comprising a rotatable sleeve coaxially surrounding the elongated shaft and configured to be rotated about a longitudinal axis defined by the elongated shaft, the rotatable sleeve defining at least one second window configured to be axially misaligned or at least partially axially aligned with the at least one first window to control fluid flow through the filter sleeve.

9. The surgical grasper according to claim 8, further comprising a rotation tab extending from the rotatable sleeve and configured for enabling a user to manually rotate the rotatable sleeve about a longitudinal axis defined by the elongated shaft.

10. The surgical grasper according to claim 1, wherein the surgical grasper is configured to be attached to a surgical robot arm of a robotic surgical system.

11. A surgical grasper configured to evacuate fluids from a surgical site, comprising:

a housing defining an interior cavity;

an elongated shaft extending distally from the housing, the elongated shaft defining a lumen in fluid communication with the interior cavity defined by the housing;

a filter sleeve disposed within the lumen defined by the elongated shaft and configured to filter fluid from a surgical site;

at least one first window extending longitudinally along at least a portion of the elongated shaft and configured to expose the filter sleeve;

an end effector including a first jaw member and a second jaw member, the first and second jaw members configured to grasp tissue;

a rotatable sleeve coaxially surrounding the elongated shaft and configured to be rotated about a longitudinal axis defined by the elongated shaft; and at least one second window extending longitudinally along at least a portion of the rotatable sleeve, wherein rotation of the rotatable sleeve is configured to rotate the at least one second window into axial misalignment with the at least one first window to prevent fluid flow through the filter sleeve or at least partial axial alignment with the at least one first window to at least partially expose the filter sleeve for facilitating fluid flow through the filter sleeve, wherein the at least partial axial alignment defines a flow path through the at least one first window, the at least one second window, and the filter sleeve.

12. The surgical grasper according to claim 11, further comprising a handle coupled to the housing and configured to pivot at least one of the first or second jaw members relative to the other jaw member to transition the end effector between a closed configuration wherein the first and second jaw members are approximated to grasp tissue and an open configuration wherein the first and second jaw members are spaced apart.

13. The surgical grasper according to claim 11, further comprising a fluid flow path extending from the filter sleeve, through the lumen defined by the elongated shaft, and through the interior cavity of the housing.

14. The surgical grasper according to claim 11, further comprising a fluid port extending from an outer surface of the housing and defining a lumen in fluid communication with the interior cavity of the housing for evacuating filtered fluid from the surgical grasper.

15. The surgical grasper according to claim 11, further comprising a rotation knob configured to rotate the end effector relative to the elongated shaft about a longitudinal axis defined by the elongated shaft.

16. The surgical grasper according to claim 11, wherein the elongated shaft, the distal cap, and the end effector are configured to be inserted through a surgical access device inserted through patient tissue to access a peritoneal cavity.

17. A surgical grasper configured to evacuate fluids from a surgical site, comprising:

a housing defining an interior cavity;

an elongated shaft extending distally from the housing and defining a lumen in fluid communication with the interior cavity defined by the housing;

a distal cap disposed at a distal end of the elongated shaft;

an end effector including a first jaw member and a second jaw member, the first and second jaw members having a distal portion configured to grasp tissue and a proximal portion pivotably coupled to the distal cap;

at least one suction hole defined through the distal cap, the at least one suction hole including an opening extending through an outer surface of the distal cap and in fluid communication with the lumen defined by the elongated shaft for evacuating fluid from a surgical site, wherein the proximal portions of the first and second jaw members are pivotably coupled to one another within the distal cap; and a filter sleeve disposed within the lumen defined by the elongated shaft and configured to filter fluid from the surgical site.

18. The surgical grasper according to claim 17, further comprising a rotatable sleeve coaxially surrounding the elongated shaft and configured to be rotated about a longitudinal axis defined by the elongated shaft to control fluid flow through the filter sleeve.

19. The surgical grasper according to claim 18, further comprising:

at least one first window extending longitudinally along at least a portion of the elongated shaft and configured to expose the filter sleeve; and at least one second window extending longitudinally along at least a portion of the rotatable sleeve, wherein rotation of the rotatable sleeve is configured to rotate the at least one second window into axial misalignment with the at least one first window to prevent fluid flow through the filter sleeve or at least partial axial alignment with the at least one first window to at least partially expose the filter sleeve for facilitating fluid flow through the filter sleeve.

20. The surgical grasper according to claim 18, further comprising a rotation tab extending from the rotatable sleeve and configured for enabling a user to manually rotate the rotatable sleeve about a longitudinal axis defined by the elongated shaft.

* * * * *